United States Patent
Nguyen (10) Patent No.: US 12,403,168 B1
(45) Date of Patent: Sep. 2, 2025

(54) METHOD FOR PRODUCING A PLANT-BASED EXTRACT COMPOSITION HAVING THE EFFECT OF ENHANCING NUTRITION AND IMMUNITY

(71) Applicant: Thuy An Thi Nguyen, Ho Chi Minh (VN)

(72) Inventor: Thuy An Thi Nguyen, Ho Chi Minh (VN)

(73) Assignee: Thuy An Thi Nguyen, Ho Chi Minh (VN)

( * ) Notice: Subject to any disclaimer, the term of this patent is extended or adjusted under 35 U.S.C. 154(b) by 0 days.

(21) Appl. No.: 19/066,076

(22) Filed: Feb. 27, 2025

(30) Foreign Application Priority Data

Dec. 30, 2024 (VN) ............................... 1-2024-09827

(51) Int. Cl.
| | | |
|---|---|---|
| *A61K 36/00* | (2006.01) | |
| *A61K 9/08* | (2006.01) | |
| *A61K 31/122* | (2006.01) | |
| *A61K 31/704* | (2006.01) | |
| *A61K 35/644* | (2015.01) | |
| *A61K 36/11* | (2006.01) | |
| *A61K 36/232* | (2006.01) | |
| *A61K 36/258* | (2006.01) | |
| *A61K 36/344* | (2006.01) | |
| *A61K 36/38* | (2006.01) | |
| *A61K 36/424* | (2006.01) | |
| *A61K 36/48* | (2006.01) | |
| *A61K 36/899* | (2006.01) | |
| *A61P 37/04* | (2006.01) | |

(52) U.S. Cl.
CPC .............. *A61K 36/258* (2013.01); *A61K 9/08* (2013.01); *A61K 31/122* (2013.01); *A61K 31/704* (2013.01); *A61K 35/644* (2013.01); *A61K 36/11* (2013.01); *A61K 36/232* (2013.01); *A61K 36/344* (2013.01); *A61K 36/38* (2013.01); *A61K 36/424* (2013.01); *A61K 36/48* (2013.01); *A61K 36/899* (2013.01); *A61P 37/04* (2018.01); *A61K 2236/13* (2013.01); *A61K 2236/15* (2013.01); *A61K 2236/17* (2013.01); *A61K 2236/333* (2013.01); *A61K 2236/35* (2013.01); *A61K 2236/39* (2013.01); *A61K 2236/51* (2013.01); *A61K 2236/53* (2013.01); *A61K 2236/55* (2013.01)

(58) Field of Classification Search
CPC ... A61K 35/644; A61K 36/258; A61K 36/232
See application file for complete search history.

(56) References Cited

PUBLICATIONS

No reference is cited.*

* cited by examiner

*Primary Examiner* — Qiuwen Mi (57) ABSTRACT

A method for producing a plant-based extract composition having the effect of enhancing nutrition and immunity comprises the following steps: (i) preparing materials; (ii) creating a base mixture; (iii) creating a foundation mixture; (iv) creating a first temporary mixture; (v) creating a second temporary mixture; (vi) creating a uniform mixture; (vii) creating a post-incubation mixture; and (viii) concentrating the post-incubation to obtain the plant-based extract composition having the effect of enhancing nutrition and immunity. This composition includes the following components: Ngoc Linh *ginseng* (*Panax vietnamensis*) extract; jiaogulan (*Gynostemma pentaphyllum*) powder; maingay's tree (*Cratoxylum maingayi*) powder; nodding clubmoss (*Lycopodiella cernua*) powder; red *ginseng* (*Radix Ginseng Rubra*) powder; codonopsis root (*Codonopsis pilosula*) powder; angelica root (*Angelica sinensis*) powder; rice bran oil, legume powder; coenzyme Q10; ginsenoside Rb1 extract; and honey.

6 Claims, 1 Drawing Sheet

METHOD FOR PRODUCING A PLANT-BASED EXTRACT COMPOSITION HAVING THE EFFECT OF ENHANCING NUTRITION AND IMMUNITY

CLAIM OF PRIORITY

This application claims priority under 35 U.S.C. § 112(d) of Application No. 1-2024-09827, filed on 30 Dec. 2024, in the Republic Socialist of Vietnam. The patent application identified above is incorporated here by reference in its entirety.

FIELD OF THE INVENTION

The invention pertains to the field of health care product manufacturing, particularly to a plant-based extract composition designed to enhance health, boost immunity, improve resistance to diseases, and promote recovery during illness. More specifically, the invention relates to a method for producing a plant-based extract composition having the effect of enhancing nutrition and immunity.

BACKGROUND ART

Protecting and enhancing the immune system is of great importance in treating autoimmune diseases, cancer, and chronic illnesses. Immunostimulants are derived from diverse sources, including biological and microbial origins. However, biologically derived immunostimulants are often expensive, while those derived from microorganisms may have unwanted side effects. There is a growing interest in developing products that enhance immunity, minimize side effects, and are cost-effective. Among these are herbal medicines and natural products known for their nutritional, anti-inflammatory, anticancer, anti-stress, and immune-boosting properties, which also help prevent oxidative damage and treat immune deficiencies. These products aim to offer alternatives with fewer side effects for patients.

Since the 1970s, scientists worldwide have been shifting towards research and development of plant-based products for community health care and protection. These products are considered highly safe, effective, free of side effects, and capable of accelerating recovery. In Vietnam, approximately 200,000 new cancer cases are reported annually, with 82,000 deaths. While the global cancer mortality rate is 59.7%, Vietnam's rate is 73.5%, one of the highest. The increasing incidence of cancer, coupled with a younger demographic, is alarming and calls for timely health protection and preventive measures.

Current cancer treatments may involve surgery, radiation therapy, chemotherapy, or a combination of these methods. The choice of treatment depends on the cancer's location, extent, patient's age, overall health, available options, and treatment goals. Common treatments, such as surgery, radiation, and chemotherapy, mainly target symptoms. They are associated with high recurrence and metastasis rates, severe side effects, and often high costs for advanced therapies like targeted and immunotherapy. These challenges underline the need for safe, effective, and affordable alternatives. Thanks to their immune-regulating properties, fatigue reduction capabilities, and anti-aging effects, plant-based products are widely used in developing health care solutions. They are often produced in various forms, such as liquid extracts, capsules, powders, and teas, which are popular for their ability to enhance immunity, regulate the immune system, and reduce the dependence on antibiotics.

Patent application No. CN115554387A relates to an immunity-enhancing and anti-fatigue composition, in which the composition includes the following ingredients: coenzyme Q10, conjugated linoleic acid, D-ribose, octacosanol, L-carnitine, calcium pyruvate, *codonopsis pilosula, radix pseudostellariae, astragalus mongholicus*, daidzein, *coptis chinensis, rheum officinale*, cinnamon, endothelium *corneum* gigeriae *galli* and hawthorn, a raw material for alleviating myasthenia gravis, an antioxidant and amino acids. In addition, the patent application No. CN115554387A also mentions the process of preparing a preparation to enhance resistance and fight fatigue, including the following steps:

a) preparation of raw materials: 10-15 kg of coenzyme Q, 2-12 kg of conjugated linoleic acid, 5-25 kg of D-ribose, 0.15-2 kg of octacosanol, 2-12 kg of L-carnitine, 2-12 kg of calcium pyruvate, 2-15 kg of *ginseng* (*Panax ginseng* C. A. Mey), 3-20 kg of *Codonopsis pilosula*, 3-20 kg of *Radix pseudostellariae*, 5-25 kg of *Astragalus membranaceus*, 2-15 kg of daidzein, 0-20 kg of kg *Coptis chinensis*, 0-20 kg *Rheum officinale*, 2-12 kg *Cinnamomum cassia*, 2-15 kg Endothelium *corneum* gigeriae *Galli*, 2-15 kg *Crataegus pinnatifida* Bunge, 5-20 kg eye fatigue relieving material, 5-20 kg antioxidant and 5-25 kg amino acid;

mix coenzyme Q10, D-ribose, octacosanol, L-carnitine, *ginseng* and daidzein to obtain material A;

mix *Pseudostellariae* root, *Codonopsis* root, *Astragalus* root, Gigeriae *Galli* endothelium, *fructus crataegi, amblyopia* relieving material, *Rhei* root and rhizome, and *Coptidis* rhizome, and mix well to obtain material B;

uniformly dry mix conjugated linoleic acid, antioxidant, calcium pyruvate, cinnamon and amino acid to obtain material C;

b) transfer the raw materials obtained in step S1 into the mixing tank through the pipeline in the order of material A, material B and material C, stir at low speed for 15-25 minutes, during which the temperature at the processing site is 15-20° C.;

c) sterilization: sterilize the powder obtained in step S2 and transfer the sterilized powder into the storage tank;

d) packaging: transfer the powder obtained in step S3 to the packaging machine, to obtain the finished product, and put it into the warehouse.

Patent application No. CN102145128A pertains to a medicinal composition for the prevention and treatment of cardiovascular and cerebrovascular diseases. The composition includes the following ingredients: blood reed 3-5 g, *ginseng* 1-3 g, *astragalus* 40-45 g, *Angelica sinensis* 9-12 g, *Cordyceps sinensis* 1-3 g, Goji berries: 10-12 g, Snow cedar root (system): 23-26 g, Chinese elm 10-12 g, jiaogulan (*Gynostemma pentaphyllum*) 10-12 g, Red sage root (*Salvia miltiorrhiza*) 20-30 g, Safflower 10-13 g, Glossy *ganoderma* (*Ganoderma lucidum*) 1-3 g, white peony root 10-12 g, *ganoderma* 23-27 g, earthworm 10-12 g, Kudzu root (*Pueraria lobata*) 23-27 g, amber 1-3 g, hawthorn 10-12 g, seaweed 10-12 g, rose flower 2-5 g, *gastrodia* rhizome (*Gastrodia elata*) 5-7 g, bear bile 1-3 g.

Patent application No. CN115088842A relates to a food product for replenishing qi, enriching blood, and calming the mind. The composition includes the following ingredients by weight: 2-3 parts of American *ginseng*, 1-3 parts of bright *Ganoderma lucidum*, 2-3 parts of *astragalus*, 1-3 parts of pseudo-*ginseng*, 1-3 parts of red sage root (*Salvia miltiorrhiza*), 2-3 parts of *poria* mushroom (*Poria cocos*), 2-3 parts of pollen, 2-3 parts of pine nuts, 2-4 parts of royal jelly and 6-8 parts of honey.

Patent application No. CN1076589A, refers to a nutritional oil with therapeutic health benefits having the following composition (weight %):

- 67.5%~100% two or more mixtures of rice bran oil, safflower oil, corn germ oil, peanut oil, sesame oil, cottonseed oil, soybean oil, rapeseed oil, palm oil, sunflower oil, olive oil, siritch oil, walnut oil, castor oil, large-fruited hodgsonia oil, hydrogenated milk thistle oil;
- 0~2.5% vitamins;
- 0~5% containing magnesium, iodine, zinc, copper, manganese, chromium, vanadium, selenium, molybdenum, sodium, potassium, chlorine, iron, calcium, phosphorus, fluorine, nickel, cobalt, silicon element compound one or more mixtures or compounds;
- 0-25% of one or more mixtures of: *ginseng*, Gastrodiae rhizomes, honeysuckle fruit, *asparagus cocos*, Chinese *magnolia* fruit, *atractylodes* rhizome, hawthorn, rhubarb, honey, *poria, angelica* (*Radix Angelicae Sinensis*), American *ginseng*, lily root, wolfberry, *eucommia* bark, royal jelly, *cordyceps sinensis, lingzhi, Radix codonopsis*, deer antler, *rehmannia glutinosa, pseudoginseng*, peony root, rainbow, pollen.

It can be seen that the above technical solutions all meet the set purposes and requirements. However, the above inventions only mention preparations used to enhance resistance and fight fatigue, replenish qi, replenish blood and calm the mind without disclosing details about the process of preparing raw materials and mixing steps to create the preparation. More specifically, the inventions do not specify the components of composition including: Ngoc Linh *ginseng* (*Panax vietnamensis*) extract, jiaogulan (*Gynostemma pentaphyllum*) powder, maingay's tree (*Cratoxylum maingayi*) powder, nodding clubmoss (*Lycopodiella cernua*) powder, red *ginseng* (*Radix Ginseng Rubra*) powder, *codonopsis* root (*Codonopsis pilosula*) powder, *angelica* root (*Angelica sinensis*) powder, rice bran oil, legume powder, coenzyme Q10, ginsenoside Rb1 extract (from *notoginseng* (*Panax notoginseng*)), and honey.

Therefore, it is necessary to create a method for producing a plant-based extract composition having the effect of enhancing nutrition and immunity, including simple, easy-to-implement steps.

It is also necessary to create a plant-based extract composition having the effect of enhancing nutrition and immunity, used to improve health, increase resistance, increase the ability to resist diseases, and increase the ability to recover from diseases.

Finally, it is also necessary to provide a method for enhancing nutrition and immunity comprising the step of dissolving a plant-based extract composition having the effect of enhancing nutrition and immunity in water to obtain a solution and administering the solution to the target subject.

SUMMARY OF THE INVENTION

Accordingly, the first aspect of the invention is to provide a method for producing a plant-based extract composition having the effect of enhancing nutrition and immunity, comprising the following steps (i) to (viii):

(i) preparing materials including:
(a) a Ngoc Linh *ginseng* (*Panax vietnamensis*) extract component having a predetermined first percentage (%) by weight, prepared by mixing a first extract and a second extract at a ratio of 2:(0.05-1) (volume/volume);

wherein the first extract is prepared by performing steps (a1) to (c1), comprising:
(a1) preparing material: collecting the Ngoc Linh *ginseng* (*Panax vietnamensis*) roots aged 3-5 years, cleaning, cutting into pieces, drying to a moisture content below 15%, grinding, and sieving through a 0.5-1 mm mesh to obtain a first powder;
(b1) extracting the first powder with saturated n-butanol (n-BuOH) solution at a ratio of 1:20 (weight/volume) for 1 hour, followed by ultrasonic-assisted extraction at a frequency of 35 kHz for 2 hours, wherein step (b1) is repeated three times to obtain a first temporary extract; and
(c1) removing the solvent from the first temporary extract and centrifuging at a speed of 1000-5000 rpm for 10 minutes to obtain the first extract;

wherein the second extract is prepared by performing steps (a2) to (d2), comprising:
(a2) preparing material: collecting the stems and leaves of the Ngoc Linh *ginseng* (*Panax vietnamensis*) aged 3-5 years, cleaning, cutting into pieces, drying to a moisture content below 15%, grinding, and sieving through a 0.5-1 mm mesh to obtain a second powder;
(b2) extracting the second powder with 70% ethanol solution at a ratio of 1:8 (weight/volume) for 2 days, then filtering to obtain a second temporary extract and a first residue;
(c2) extracting the first residue with 70% ethanol solution at a ratio of 1:2 (weight/volume) using ultrasonic-assisted extraction at a frequency of 35 kHz for 3 hours, then filtering to obtain a third temporary extract; and
(d2) mixing the second temporary extract with the third temporary extract, removing the solvent, and filtering to obtain the second extract;

(b) a jiaogulan (*Gynostemma pentaphyllum*) powder component having a predetermined second percentage (%) by weight, prepared by cleaning the leaves and stems, cold-drying at 30° C.-31° C. until the moisture reaches 5%-7%, then grinding and sieving through a 0.5-1 mm mesh to obtain the jiaogulan (*Gynostemma pentaphyllum*) powder component;

(c) a maingay's tree (*Cratoxylum maingayi*) powder component having a predetermined third percentage (%) by weight, prepared by cleaning the leaves, drying at 50° C.-60° C. until the moisture reaches 5%-7%, then grinding and sieving through a 0.5-1 mm mesh to obtain the maingay's tree (*Cratoxylum maingayi*) powder component;

(d) a nodding clubmoss (*Lycopodiella cernua*) powder component having a predetermined fourth percentage (%) by weight, prepared by cleaning the entire plant, drying at 50° C.-60° C. until the moisture reaches 5%-7%, then grinding and sieving through a 0.5-1 mm mesh to obtain the nodding clubmoss (*Lycopodiella cernua*) powder component;

(e) a red *ginseng* (*Radix Ginseng Rubra*) powder component having a predetermined fifth percentage (%) by weight, prepared by cleaning the roots, drying in three stages (at 40° C. for 24 hours, at 50° C. for 48 hours, and at 60° C. until the moisture reaches 5%-7%), then grinding and sieving through a 0.5-1 mm mesh to obtain the red *ginseng* (*Radix Ginseng Rubra*) powder component;

(f) a *codonopsis* root (*Codonopsis pilosula*) powder component having a predetermined sixth percentage (%) by weight, prepared by cleaning the roots, cutting into 0.5-1 cm pieces, drying at 60° C. until the moisture reaches 5%-7%, then grinding and sieving through a 0.5-1 mm mesh to obtain the *codonopsis* root (*Codonopsis pilosula*) powder component;

(g) an *angelica* root (*Angelica sinensis*) powder component having a predetermined seventh percentage (%) by weight, prepared by cleaning the roots, drying at 30° C.-35° C. until the moisture reaches 5%-7%, then grinding and sieving through a 0.5-1 mm mesh to obtain the *angelica* root (*Angelica sinensis*) powder component;

(h) a rice bran oil component having a predetermined eighth percentage (%) by weight, extracted from the germ and inner bran layer of rice using water-assisted ultrasonic extraction at 50° C. for 30 minutes with a stirring speed of 1000 rpm and a rice bran-to-water ratio of 1.5:10; ultrasonic treatment is conducted for 70 minutes at 25° C. to obtain the rice bran oil component;

(i) a legume powder component having a predetermined ninth percentage (%) by weight, including 1 part red bean (*Vigna angularis*), 1 part black bean (*Vigna cylindrica*), 1 part green bean (*Vigna radiata*), 1 part soybean (*Glycine max*), and 1 part white bean (*Vigna unguiculata*);

(j) a coenzyme Q10 component having a predetermined tenth percentage (%) by weight, extracted from a royal jelly (*Apis cerana*) by performing steps (A) to (F):

(A) preparing the royal jelly obtained from honeybees (*Apis cerana*) selected from one or more species with genbank identifiers including: KM066965.1, KM066964.1, KM066963.1, KM066960.1, KM066951.1, KM066962.1, KM066959.1, KM066957.1, KM066961.1, KM066952.1, KM066955.1, KM066956.1, KM066958.1, KM066953.1, and KM066954.1;

(B) mixing 0.5 g of the royal jelly with 1 mL of methanol and 1 mL of n-hexane in a 10 mL test tube, shaking the test tube for 2 minutes, and subjecting it to ultrasonic treatment at a frequency of 35 kHz for 30 minutes to obtain a mixed solution;

(C) centrifuging the mixed solution at 2500 rpm for 15 minutes, then filtering to obtain a filtered solution;

(D) centrifuging the filtered solution for 5 minutes at 4500 rpm to obtain a first solution;

(E) mixing the first solution with 1 mL of n-hexane and another 1 mL of n-hexane in a 10 mL test tube, shaking the test tube for 2 minutes, and subjecting it to ultrasonic treatment at a frequency of 35 kHz for 30 minutes, repeating step (E) twice to obtain a second solution; and (F) concentrating the second solution using inert gas (nitrogen) to obtain the coenzyme Q10 component;

(k) a ginsenoside Rb1 extract component having a predetermined eleventh percentage (%) by weight, prepared by performing steps (a3) to (g3), including:

(a3) preparing material: obtaining a *notoginseng* (*Panax notoginseng*) roots aged 3 to 7 years, washing them clean, cutting into small pieces, and drying to a moisture content of less than 15%;

(b3) extracting the material with 60% ethanol solvent at a ratio of 1:6 (weight/volume) using an ultrasonic extraction device at 60° C. for 2 hours, repeating step (b3) three times to obtain a fourth temporary extract;

(c3) filtering the fourth temporary extract and removing the solvent to obtain an extract concentrate;

(d3) dissolving the extract concentrate in distilled water at a ratio of 1:6 (weight/volume) to obtain a fifth temporary extract;

(e3) adding n-butanol solution and the fifth temporary extract at a ratio of 2:1 (volume/volume) to an ultrasonic extraction device at 60° C. for 2 hours, repeating step (e3) three times to obtain a n-butanol fraction and distilling the solvent under reduced pressure to obtain a sixth temporary extract;

(f3) centrifuging the sixth temporary extract at 5000 rpm for 10 minutes to obtain a precipitate; and (g3) drying the precipitate at 75° C. for 3-8 hours to obtain the ginsenoside Rb1 extract component;

(l) the remainder is a honey component having a predetermined twelfth percentage (%) by weight;

wherein the total weight percentage from the first to the twelfth components equals 100% by weight;

(ii) creating a base mixture by heating the honey component at 60° C.-65° C., stirring at 300-500 rpm for 30 minutes;

(iii) creating a foundation mixture by homogenizing the rice bran oil with the base mixture at step (ii), stirring at 300-500 rpm, and heating for an additional 2-5 minutes;

(iv) mixing the components (a) to (g) in order with the foundation mixture at step (iii) to create a first temporary mixture, ensuring homogeneous mixing after each addition;

(v) mixing the legume powder component with the first temporary mixture at step (iv) at 300-500 rpm for 20 minutes to create a second temporary mixture;

(vi) mixing the coenzyme Q10 component with the second temporary mixture at step (v) at 300-500 rpm for 20 minutes to obtain a uniform mixture;

(vii) incubating the uniform mixture at 25° C.-37° C. for 10-15 days, adding the ginsenoside Rb1 extract component, and continuing incubation at 25° C.-37° C. for 10-15 days to obtain a post-incubation mixture; and (viii) concentrating the post-incubation mixture at 50° C. to obtain the plant-based extract composition having the effect of enhancing nutrition and immunity.

The second aspect of the invention is to provide a plant-based extract composition having the effect of enhancing nutrition and immunity comprising: a Ngoc Linh *ginseng* (*Panax vietnamensis*) extract component having a predetermined first percentage (%) by weight, a jiaogulan (*Gynostemma pentaphyllum*) powder component having a predetermined second percentage (%) by weight, a maingay's tree (*Cratoxylum maingayi*) powder component having a predetermined third percentage (%) by weight, a nodding clubmoss (*Lycopodiella cernua*) powder component having a predetermined fourth percentage (%) by weight, a red *ginseng* (*Radix Ginseng Rubra*) powder component having a predetermined fifth percentage (%) by weight, a *codonopsis* root (*Codonopsis pilosula*) powder component having a predetermined sixth percentage (%) by weight, an *angelica* root (*Angelica sinensis*) powder component having a predetermined seventh percentage (%) by weight, a rice bran oil component having a predetermined eighth percentage (%) by weight, a legume powder component having a predetermined ninth percentage (%) by weight, a coenzyme Q10 component having a predetermined tenth percentage (%) by weight, a ginsenoside Rb1 extract component having a predetermined eleventh percentage (%) by weight, and the remainder is a honey component having a predetermined twelfth percentage (%) by weight.

The third aspect of the invention is to provide a plant-based extract composition having the effect of enhancing nutrition and immunity comprising: the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) by weight to make up 100%.

The fourth aspect of the invention is to provide a plant-based extract composition having the effect of enhancing nutrition and immunity comprising: the predetermined first percentage (%) by weight is 0.5%-1%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) by weight to make up 100%.

The fifth aspect of the invention is to provide a plant-based extract composition having the effect of enhancing nutrition and immunity comprising: the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 8%-10%, the predetermined eleventh percentage (%) by weight is 1.5%-2%, and the remainder is the twelfth percentage (%) by weight to make up 100%.

The sixth aspect of the invention is to provide a plant-based extract composition having the effect of enhancing nutrition and immunity comprising: the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 12%-13%, the predetermined eleventh percentage (%) by weight is 1.5%-2%, and the remainder is the twelfth percentage (%) by weight to make up 100%.

The seventh aspect of the invention is to provide a plant-based extract composition having the effect of enhancing nutrition and immunity comprising: the predetermined first percentage (%) by weight is 1.2%-1.4%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) by weight to make up 100%.

Finally, the eighth aspect of the invention is to provide a method for enhancing nutrition and immunity comprising the step of dissolving a plant-based extract composition having the effect of enhancing nutrition and immunity in water to obtain a solution and administering the solution to the target subject.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skills in the art that the present invention may be practiced without these specific details. In other instances, well-known methods, procedures, components, and circuits have not been described in detail so as not to unnecessarily obscure aspects of the present invention.

According to the invention, the percentage (%) by weight or weight percentage (%) is expressed as a percentage of the weight of a component relative to the total weight of all components, represented as w/w (%). The percentage (%) by weight of a component is calculated as follows: weight percentage or weight (%) of a component=(weight of the component÷total weight of all components)×100%. In this calculation, the units are typically measured in grams (denoted as g) or kilograms (denoted as kg).

Figure 1:
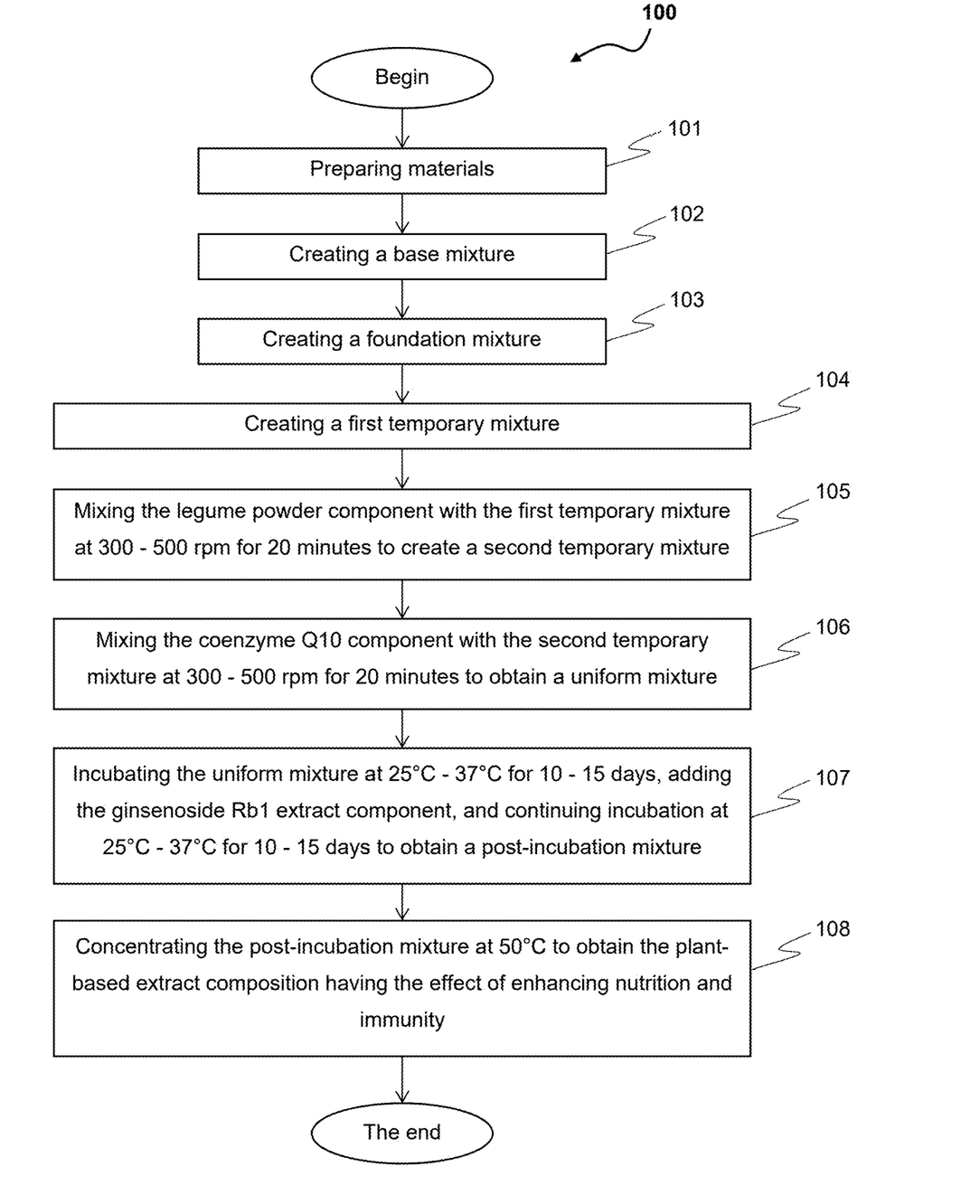
FIG. 1 is a flowchart illustrating a method for producing a plant-based extract composition having the effect of enhancing nutrition and immunity.

Now, referring to FIG. 1, a method for producing a plant-based extract composition having the effect of enhancing nutrition and immunity 100 ("method 100") according to the embodiment of the invention is described. Method 100 begins with step 101, preparing materials including: (a) a Ngoc Linh *ginseng* (*Panax vietnamensis*) extract component having a predetermined first percentage (%) by weight; (b) a jiaogulan (*Gynostemma pentaphyllum*) powder component having a predetermined second percentage (%) by weight; (c) a maingay's tree (*Cratoxylum maingayi*) powder component having a predetermined third percentage (%) by weight; (d) a nodding clubmoss (*Lycopodiella cernua*) powder component having a predetermined fourth percentage (%) by weight; (e) a red *ginseng* (*Radix Ginseng Rubra*) powder component having a predetermined fifth percentage (%) by weight; (f) a *codonopsis* root (*Codonopsis pilosula*) powder component having a predetermined sixth percentage (%) by weight; (g) an *angelica* root (*Angelica sinensis*) powder component having a predetermined seventh percentage (%) by weight; (h) a rice bran oil component having a predetermined eighth percentage (%) by weight; (i) a legume powder component having a predetermined ninth percentage (%) by weight; (j) a coenzyme Q10 component having a predetermined tenth percentage (%) by weight, (k) a ginsenoside Rb1 extract component having a predetermined eleventh percentage (%) by weight, (l) and the remainder is a honey component having a predetermined twelfth percentage (%) by weight.

In the present invention, (a) the Ngoc Linh *ginseng* (*Panax vietnamensis*) extract component having a predetermined first percentage (%) by weight, prepared by mixing a first extract and a second extract at a ratio of 2:(0.05-1) (volume/volume);
  wherein the first extract is prepared by performing steps (a1) to (c1), comprising:
    (a1) preparing material: collecting the Ngoc Linh *ginseng* (*Panax vietnamensis*) roots aged 3-5 years, cleaning, cutting into pieces, drying to a moisture content below 15%, grinding, and sieving through a 0.5-1 mm mesh to obtain a first powder;
    (b1) extracting the first powder with saturated n-butanol (n-BuOH) solution at a ratio of 1:20 (weight/volume) for 1 hour, followed by ultrasonic-assisted extraction at a frequency of 35 kHz for 2 hours, wherein step (b1) is repeated three times to obtain a first temporary extract; and
    (c1) removing the solvent from the first temporary extract and centrifuging at a speed of 1000-5000 rpm for 10 minutes to obtain the first extract;
  wherein the second extract is prepared by performing steps (a2) to (d2), comprising:
    (a2) preparing material: collecting the stems and leaves of the Ngoc Linh *ginseng* (*Panax vietnamensis*) aged 3-5 years, cleaning, cutting into pieces, drying to a moisture content below 15%, grinding, and sieving through a 0.5-1 mm mesh to obtain a second powder;
    (b2) extracting the second powder with 70% ethanol solution at a ratio of 1:8 (weight/volume) for 2 days, then filtering to obtain a second temporary extract and a first residue;
    (c2) extracting the first residue with 70% ethanol solution at a ratio of 1:2 (weight/volume) using ultrasonic-assisted extraction at a frequency of 35 kHz for 3 hours, then filtering to obtain a third temporary extract; and
    (d2) mixing the second temporary extract with the third temporary extract, removing the solvent, and filtering to obtain the second extract;

In the present invention, (b) the jiaogulan (*Gynostemma pentaphyllum*) powder component having a predetermined second percentage (%) by weight, prepared by cleaning the leaves and stems, cold-drying at 30° C.-31° C. until the moisture reaches 5%-7%, then grinding and sieving through a 0.5-1 mm mesh to obtain the jiaogulan (*Gynostemma pentaphyllum*) powder component.

In the present invention, (c) the maingay's tree (*Cratoxylum maingayi*) powder component having a predetermined third percentage (%) by weight, prepared by cleaning the leaves, drying at 50° C.-60° C. until the moisture reaches 5%-7%, then grinding and sieving through a 0.5-1 mm mesh to obtain the maingay's tree (*Cratoxylum maingayi*) powder component.

In the present invention, (d) the nodding clubmoss (*Lycopodiella cernua*) powder component having a predetermined fourth percentage (%) by weight, prepared by cleaning the entire plant, drying at 50° C.-60° C. until the moisture reaches 5%-7%, then grinding and sieving through a 0.5-1 mm mesh to obtain the nodding clubmoss (*Lycopodiella cernua*) powder component.

In the present invention, (e) the red *ginseng* (*Radix Ginseng Rubra*) powder component having a predetermined fifth percentage (%) by weight, prepared by cleaning the roots, drying in three stages (at 40° C. for 24 hours, at 50° C. for 48 hours, and at 60° C. until the moisture reaches 5%-7%), then grinding and sieving through a 0.5-1 mm mesh to obtain the red *ginseng* (*Radix Ginseng Rubra*) powder component.

In the present invention, (f) the *codonopsis* root (*Codonopsis pilosula*) powder component having a predetermined sixth percentage (%) by weight, prepared by cleaning the roots, cutting into 0.5-1 cm pieces, drying at 60° C. until the moisture reaches 5%-7%, then grinding and sieving through a 0.5-1 mm mesh to obtain the *codonopsis* root (*Codonopsis pilosula*) powder component.

In the present invention, (g) the *angelica* root (*Angelica sinensis*) powder component having a predetermined seventh percentage (%) by weight, prepared by cleaning the roots, drying at 30° C.-35° C. until the moisture reaches 5%-7%, then grinding and sieving through a 0.5-1 mm mesh to obtain the *angelica* root (*Angelica sinensis*) powder component.

In the present invention, (h) the rice bran oil component having a predetermined eighth percentage (%) by weight, extracted from the germ and inner bran layer of rice using water-assisted ultrasonic extraction at 50° C. for 30 minutes with a stirring speed of 1000 rpm and a rice bran-to-water ratio of 1.5:10; ultrasonic treatment is conducted for 70 minutes at 25° C. to obtain the rice bran oil component.

In the present invention, (i) the legume powder component having a predetermined ninth percentage (%) by weight, including 1 part red bean (*Vigna angularis*), 1 part black bean (*Vigna cylindrica*), 1 part green bean (*Vigna radiata*), 1 part soybean (*Glycine max*), and 1 part white bean (*Vigna unguiculata*).

In the present invention, (j) the coenzyme Q10 component having a predetermined tenth percentage (%) by weight, extracted from a royal jelly (*Apis cerana*) by performing steps (A) to (F):
- (A) preparing the royal jelly obtained from honeybees (*Apis cerana*) selected from one or more species with genbank identifiers including: KM066965.1, KM066964.1, KM066963.1, KM066960.1, KM066951.1, KM066962.1, KM066959.1, KM066957.1, KM066961.1, KM066952.1, KM066955.1, KM066956.1, KM066958.1, KM066953.1, and KM066954.1;
- (B) mixing 0.5 g of the royal jelly with 1 mL of methanol and 1 mL of n-hexane in a 10 mL test tube, shaking the test tube for 2 minutes, and subjecting it to ultrasonic treatment at a frequency of 35 kHz for 30 minutes to obtain a mixed solution;
- (C) centrifuging the mixed solution at 2500 rpm for 15 minutes, then filtering to obtain a filtered solution;
- (D) centrifuging the filtered solution for 5 minutes at 4500 rpm to obtain a first solution;
- (E) mixing the first solution with 1 mL of n-hexane and another 1 mL of n-hexane in a 10 mL test tube, shaking the test tube for 2 minutes, and subjecting it to ultrasonic treatment at a frequency of 35 kHz for 30 minutes, repeating step (E) twice to obtain a second solution; and
- (F) concentrating the second solution using inert gas (nitrogen) to obtain the coenzyme Q10 component.

In the present invention, (k) the ginsenoside Rb1 extract component having a predetermined eleventh percentage (%) by weight, prepared by performing steps (a3) to (g3), including:
- (a3) preparing material: obtaining a *notoginseng* (*Panax notoginseng*) roots aged 3 to 7 years, washing them clean, cutting into small pieces, and drying to a moisture content of less than 15%;
- (b3) extracting the material with 60% ethanol solvent at a ratio of 1:6 (weight/volume) using an ultrasonic extraction device at 60° C. for 2 hours, repeating step (b3) three times to obtain a fourth temporary extract;
- (c3) filtering the fourth temporary extract and removing the solvent to obtain an extract concentrate;
- (d3) dissolving the extract concentrate in distilled water at a ratio of 1:6 (weight/volume) to obtain a fifth temporary extract;
- (e3) adding n-butanol solution and the fifth temporary extract at a ratio of 2:1 (volume/volume) to an ultrasonic extraction device at 60° C. for 2 hours, repeating step
- (e3) three times to obtain a n-butanol fraction and distilling the solvent under reduced pressure to obtain a sixth temporary extract;
- (f3) centrifuging the sixth temporary extract at 5000 rpm for 10 minutes to obtain a precipitate; and
- (g3) drying the precipitate at 75° C. for 3-8 hours to obtain the ginsenoside Rb1 extract component.

In the present invention, (l) the remainder is the honey component having a predetermined twelfth percentage (%) by weight.

In the present invention, the total weight percentage from the first to the twelfth components equals 100% by weight.

At step 102, creating a base mixture by heating the honey component at 60° C.-65° C., stirring at 300-500 rpm for 30 minutes.

At step 103, creating a foundation mixture by homogenizing the rice bran oil with the base mixture at step (ii), stirring at 300-500 rpm, and heating for an additional 2-5 minutes.

At step 104, mixing the components (a) to (g) in order with the foundation mixture at step (iii) to create a first temporary mixture, ensuring homogeneous mixing after each addition.

At step 105, mixing the legume powder component with the first temporary mixture at step (iv) at 300-500 rpm for 20 minutes to create a second temporary mixture.

At step 106, mixing the coenzyme Q10 component with the second temporary mixture at step (v) at 300-500 rpm for 20 minutes to obtain a uniform mixture.

Within the scope of the invention, the term "uniform mixture" encompasses the following meanings:
- (a') the uniform mixture refers to a mixture in which the material components (a)-(g) are fully dissolved into the base mixture at precise weight percentage (%) ratios; and
- (b') the uniform mixture functions as a reactive medium, enabling the addition of component (k) the ginsenoside Rb1 extract component from the *notoginseng* (*Panax notoginseng*) roots, which possesses specific chemical and physical properties to create the plant-based extract composition having the effect of enhancing nutrition and immunity.

At step 107, incubating the uniform mixture at 25° C.-37° C. for 10-15 days, adding the ginsenoside Rb1 extract component, and continuing incubation at 25° C.-37° C. for 10-15 days to obtain a post-incubation mixture.

Finally, at step 108, concentrating the post-incubation mixture at 50° C. to obtain the plant-based extract composition having the effect of enhancing nutrition and immunity.

In the present invention, steps 101 to 106 are carried out using a magnetic stirrer, a mechanical stirrer, or a stirring device, all of which are known in the prior art. Therefore, the structure and operating principles of these devices will not be described in detail in this invention.

According to another embodiment of the invention, a plant-based extract composition having the effect of enhancing nutrition and immunity 200 ("composition 200") obtained from method 100 comprising: a Ngoc Linh *ginseng* (*Panax vietnamensis*) extract component having a predetermined first percentage (%) by weight, a jiaogulan (*Gynostemma pentaphyllum*) powder component having a predetermined second percentage (%) by weight, a maingay's tree (*Cratoxylum maingayi*) powder component having a predetermined third percentage (%) by weight, a nodding clubmoss (*Lycopodiella cernua*) powder component having a predetermined fourth percentage (%) by weight, a red *ginseng* (*Radix Ginseng Rubra*) powder component having a predetermined fifth percentage (%) by weight, a *codonopsis* root (*Codonopsis pilosula*) powder component having a predetermined sixth percentage (%) by weight, an *angelica* root (*Angelica sinensis*) powder component having a predetermined seventh percentage (%) by weight, a rice bran oil component having a predetermined eighth percentage (%) by weight, a legume powder component having a predetermined ninth percentage (%) by weight, a coenzyme Q10 component having a predetermined tenth percentage (%) by weight, a ginsenoside Rb1 extract component having a predetermined eleventh percentage (%) by weight, and the remainder is a honey component having a predetermined twelfth percentage (%) by weight.

According to the preferred embodiment of the present invention, composition 200 comprising: the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) by weight to make up 100%.

According to the preferred embodiment of the present invention, composition 200 comprising: the predetermined first percentage (%) by weight is 0.5%-1%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) by weight to make up 100%.

According to the preferred embodiment of the present invention, composition 200 comprising: the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 8%-10%, the predetermined eleventh percentage (%) by weight is 1.5%-2%, and the remainder is the twelfth percentage (%) by weight to make up 100%.

According to the preferred embodiment of the present invention, composition 200 comprising: the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 12%-13%, the predetermined eleventh percentage (%) by weight is 1.5%-2%, and the remainder is the twelfth percentage (%) by weight to make up 100%.

According to the preferred embodiment of the present invention, composition 200 comprising: the predetermined first percentage (%) by weight is 1.2%-1.4%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) by weight to make up 100%.

TABLE 1

Components for producing composition 200 obtained from method 100 according to the embodiment of the invention

| No. | Components | Percentage (%) | Percentage (%) | Percentage (%) | Percentage (%) | Percentage (%) |
|---|---|---|---|---|---|---|
| (a) | The Ngoc Linh ginseng (*Panax vietnamensis*) extract component | 1.5%-2% | 0.5%-1% | 1.5%-2% | 1.5%-2% | 1.2%-1.4% |
| (b) | The jiaogulan (*Gynostemma pentaphyllum*) powder component | 1.5%-2% | 1.5%-2% | 1.5%-2% | 1.5%-2% | 1.5%-2% |
| (c) | The maingay's tree (*Cratoxylum maingayi*) powder component | 1.5%-2% | 1.5%-2% | 1.5%-2% | 1.5%-2% | 1.5%-2% |
| (d) | The nodding clubmoss (*Lycopodiella cernua*) powder component | 1.5%-2% | 1.5%-2% | 1.5%-2% | 1.5%-2% | 1.5%-2% |
| (e) | The red ginseng (*Radix Ginseng Rubra*) powder component | 1.5%-2% | 1.5%-2% | 1.5%-2% | 1.5%-2% | 1.5%-2% |
| (f) | The codonopsis root (*Codonopsis pilosula*) powder component | 1.5%-2% | 1.5%-2% | 1.5%-2% | 1.5%-2% | 1.5%-2% |

TABLE 1-continued

Components for producing composition 200 obtained from method 100 according to the embodiment of the invention

| No. | Components | Percentage (%) | Percentage (%) | Percentage (%) | Percentage (%) | Percentage (%) |
|---|---|---|---|---|---|---|
| (g) | The angelica root (*Angelica sinensis*) powder component | 1.5%-2% | 1.5%-2% | 1.5%-2% | 1.5%-2% | 1.5%-2% |
| (h) | The rice bran oil component | 15%-20% | 15%-20% | 15%-20% | 15%-20% | 15%-20% |
| (i) | The legume powder component | 15%-20% | 15%-20% | 15%-20% | 15%-20% | 15%-20% |
| (j) | The coenzyme Q10 component | 15%-20% | 15%-20% | 8%-10%. | 12%-13% | 15%-20% |
| (k) | The ginsenoside Rb1 extract component | 1.5%-2% | 1.5%-2% | 1.5%-2% | 1.5%-2% | 1.5%-2% |
| (l) | The honey component | Remaining percent | Remaining percent | Remaining percent | Remaining percent | Remaining percent |

In the present invention, a method for enhancing nutrition and immunity comprising the step of dissolving composition 200 obtained from method 100 in water to obtain a solution and administering the solution to the target subject.

In this embodiment of the invention, composition 200 obtained from method 100 meets the sensory, quality, and safety standards, all of which are listed in Tables 2 and 3 below.

TABLE 2

Sensory and quality criteria of composition 200 obtained from method 100 according to the embodiment of the invention

| No. | Criteria | Composition 200 |
|---|---|---|
| 1 | State | Thick extract |
| 2 | Color | Dark brown |
| 3 | Odor and taste | Characteristic aroma and flavor from the harmonious blend of ingredients |
| 4 | Moisture content | Greater than 40% |
| 5 | Ash content | 4%-5% |

TABLE 3

Safety criteria of composition 200 obtained from method 100 according to the embodiment of the invention

| No. | Criteria | Unit |
|---|---|---|
| 1 | Arsenic (As) | Not detected |
| 2 | Cadmium (Cd) | Not detected |
| 3 | Lead (Pb) | Not detected |
| 4 | Mercury (Hg) | Not detected |
| 5 | Total aerobic microorganisms | Not detected |
| 6 | Total yeast and mold | Not detected |
| 7 | Coliform | Not detected |
| 8 | *E. coli* | Not detected |
| 9 | *Salmonella*/25 g | Not detected |

The invention provides a method for producing a plant-based extract composition having the effect of enhancing nutrition and immunity. This method involves simple, easy-to-implement steps, enabling the efficient production of high-quality compositions while effectively utilizing natural resources.

The invention also provides a plant-based extract composition that improves nutrition, boosts immunity, and supports disease treatment.

The example is made according to the embodiment of the present invention, the composition 200 is created by process 100 including five examples listed in Table 4 below.

TABLE 4

Mixed ingredients of the composition 200 according five examples in accordance with exemplary embodiment of the present invention

| | | Unit | | | | |
|---|---|---|---|---|---|---|
| No. | Name of | Example 1 | Example 2 | Example 3 | Example 4 | Example 5 |
| (a) | The Ngoc Linh ginsen (*Panax vietnamensis*) extract component | 50 L | 25 L | 50 L | 50 L | 37.5 L |
| (b) | The jiaogulan (*Gynostemma pentaphyllum*) powder component | 50 kg | 50 kg | 50 kg | 50 kg | 50 kg |
| (c) | The maingay's tree (*Cratoxylum maingayi*) powder component | 50 kg | 50 kg | 50 kg | 50 kg | 50 kg |
| (d) | The nodding clubmoss (*Lycopodiella cernua*) powder component | 50 kg | 50 kg | 50 kg | 50 kg | 50 kg |

TABLE 4-continued

Mixed ingredients of the composition 200 according five examples in accordance with exemplary embodiment of the present invention

|     |                                                              | Unit         |              |              |              |              |
| --- | ------------------------------------------------------------ | ------------ | ------------ | ------------ | ------------ | ------------ |
| No. | Name of                                                      | Example 1    | Example 2    | Example 3    | Example 4    | Example 5    |
| (e) | The red ginseng (*Radix Ginseng Rubra*) powder component     | 50 kg        | 50 kg        | 50 kg        | 50 kg        | 50 kg        |
| (f) | The codonopsis root (*Codonopsis pilosula*) powder component | 50 kg        | 50 kg        | 50 kg        | 50 kg        | 50 kg        |
| (g) | The angelica root (*Angelica sinensis*) powder component     | 50 kg        | 50 kg        | 50 kg        | 50 kg        | 50 kg        |
| (h) | The rice bran oil component                                  | 500 L        | 500 L        | 500 L        | 500 L        | 500 L        |
| (i) | The legume powder component                                  | 500 kg       | 500 kg       | 500 kg       | 500 kg       | 500 kg       |
| (j) | The coenzyme Q10 component                                   | 500 L        | 500 L        | 250 L        | 375 L        | 500 L        |
| (k) | The ginsenoside Rb1 extract component                        | 50 L         | 50 L         | 50 L         | 50 L         | 50 L         |
| (l) | The honey component                                          | rest         | rest         | rest         | rest         | rest         |

The example 1 is made according to the embodiment of the present invention, the composition 200 is created by process 100 comprising:

(I) preparing materials including:
  (a) a Ngoc Linh *ginseng* (*Panax vietnamensis*) extract component prepared by mixing a first extract and a second extract at a ratio of 2:1;
  wherein the first extract is prepared by performing steps (a1) to (c1), comprising:
    (a1) preparing material: collecting the Ngoc Linh *ginseng* (*Panax vietnamensis*) roots aged 3-5 years, cleaning, cutting into pieces, drying to a moisture content below 15%, grinding, and sieving through a 0.5 mm mesh to obtain a first powder;
    (b1) extracting the first powder with saturated n-butanol solution at a ratio of 1:20 (weight/volume) for 1 hour, followed by ultrasonic-assisted extraction at a frequency of 35 kHz for 2 hours, wherein step (b1) is repeated three times to obtain a first temporary extract; and
    (c1) removing the solvent from the first temporary extract and centrifuging at a speed of 1000-5000 rpm for 10 minutes to obtain the first extract;
  wherein the second extract is prepared by performing steps (a2) to (d2), comprising:
    (a2) preparing material: collecting the stems and leaves of the Ngoc Linh *ginseng* (*Panax vietnamensis*) aged 3-5 years, cleaning, cutting into pieces, drying to a moisture content below 15%, grinding, and sieving through a 0.5-1 mm mesh to obtain a second powder;
    (b2) extracting the second powder with 70% ethanol solution at a ratio of 1:8 (weight/volume) for 2 days, then filtering to obtain a second temporary extract and a first residue;
    (c2) extracting the first residue with 70% ethanol solution at a ratio of 1:2 (weight/volume) using ultrasonic-assisted extraction at a frequency of 35 kHz for 3 hours, then filtering to obtain a third temporary extract; and
    (d2) mixing the second temporary extract with the third temporary extract, removing the solvent, and filtering to obtain the second extract;
  (b) a jiaogulan (*Gynostemma pentaphyllum*) powder component prepared by cleaning the leaves and stems, cold-drying at 30° C.-31° C. until the moisture reaches 5%-7%, then grinding and sieving through a 0.5-1 mm mesh to obtain the jiaogulan (*Gynostemma pentaphyllum*) powder component;
  (c) a maingay's tree (*Cratoxylum maingayi*) powder component prepared by cleaning the leaves, drying at 55° C. until the moisture reaches 6%, then grinding and sieving through a 0.5 mm mesh to obtain the maingay's tree (*Cratoxylum maingayi*) powder component;
  (d) a nodding clubmoss (*Lycopodiella cernua*) powder component prepared by cleaning the entire plant, drying at 55° C. until the moisture reaches 6%, then grinding and sieving through a 0.5 mm mesh to obtain the nodding clubmoss (*Lycopodiella cernua*) powder component;
  (e) a red *ginseng* (*Radix Ginseng Rubra*) powder component prepared by cleaning the roots, drying in three stages (at 40° C. for 24 hours, at 50° C. for 48 hours, and at 60° C. until the moisture reaches 6%, then grinding and sieving through a 0.5 mm mesh to obtain the red *ginseng* (*Radix Ginseng Rubra*) powder component;
  (f) a *codonopsis* root (*Codonopsis pilosula*) powder component prepared by cleaning the roots, cutting into 1 cm pieces, drying at 60° C. until the moisture reaches 6%, then grinding and sieving through a 0.5 mm mesh to obtain the *codonopsis* root (*Codonopsis pilosula*) powder component;
  (g) an angelica root (*Angelica sinensis*) powder component prepared by cleaning the roots, drying at 35° C. until the moisture reaches 6%, then grinding and sieving through a 0.5 mm mesh to obtain the angelica root (*Angelica sinensis*) powder component;
  (h) a rice bran oil component extracted from the germ and inner bran layer of rice using water-assisted ultrasonic extraction at 50° C. for 30 minutes with a stirring speed of 1000 rpm and a rice bran-to-water ratio of 1.5:10; ultrasonic treatment is conducted for 70 minutes at 25° C. to obtain the rice bran oil component;

(i) a legume powder component including 1 part red bean (*Vigna angularis*), 1 part black bean (*Vigna cylindrica*), 1 part green bean (*Vigna radiata*), 1 part soybean (*Glycine max*), and 1 part white bean (*Vigna unguiculata*);

(j) a coenzyme Q10 component extracted from a royal jelly (*Apis cerana*) by performing steps (A) to (F):
  (A) preparing the royal jelly obtained from honeybees (*Apis cerana*) selected from one or more species with genbank identifiers including: KM066965.1, KM066964.1, KM066963.1, KM066960.1, KM066951.1, KM066962.1, KM066959.1, KM066957.1, KM066961.1, KM066952.1, KM066955.1, KM066956.1, KM066958.1, KM066953.1, and KM066954.1;
  (B) mixing 0.5 g of the royal jelly with 1 mL of methanol and 1 mL of n-hexane in a 10 mL test tube, shaking the test tube for 2 minutes, and subjecting it to ultrasonic treatment at a frequency of 35 kHz for 30 minutes to obtain a mixed solution;
  (C) centrifuging the mixed solution at 2500 rpm for 15 minutes, then filtering to obtain a filtered solution;
  (D) centrifuging the filtered solution for 5 minutes at 4500 rpm to obtain a first solution;
  (E) mixing the first solution with 1 mL of n-hexane and another 1 mL of n-hexane in a 10 mL test tube, shaking the test tube for 2 minutes, and subjecting it to ultrasonic treatment at a frequency of 35 kHz for 30 minutes, repeating step (E) twice to obtain a second solution; and
  (F) concentrating the second solution using inert gas (nitrogen) to obtain the coenzyme Q10 component;

(k) a ginsenoside Rb1 extract component prepared by performing steps (a3) to (g3), including:
  (a3) preparing material: obtaining a *notoginseng* (*Panax notoginseng*) roots aged 3 to 7 years, washing them clean, cutting into small pieces, and drying to a moisture content of less than 15%;
  (b3) extracting the material with 60% ethanol solvent at a ratio of 1:6 (weight/volume) using an ultrasonic extraction device at 60° C. for 2 hours, repeating step (b3) three times to obtain a fourth temporary extract;
  (c3) filtering the fourth temporary extract and removing the solvent to obtain an extract concentrate;
  (d3) dissolving the extract concentrate in distilled water at a ratio of 1:6 (weight/volume) to obtain a fifth temporary extract;
  (e3) adding n-butanol solution and the fifth temporary extract at a ratio of 2:1 (volume/volume) to an ultrasonic extraction device at 60° C. for 2 hours, repeating step (e3) three times to obtain a n-butanol fraction and distilling the solvent under reduced pressure to obtain a sixth temporary extract;
  (f3) centrifuging the sixth temporary extract at 5000 rpm for 10 minutes to obtain a precipitate; and
  (g3) drying the precipitate at 75° C. for 3-8 hours to obtain the ginsenoside Rb1 extract component;

(I) the remainder is a honey component;
(II) creating a base mixture by heating the honey component at 60° C., stirring at 400 rpm for 30 minutes;
(III) creating a foundation mixture by homogenizing the rice bran oil with the base mixture, stirring at 400 rpm, and heating for an additional 3 minutes;
(IV) mixing in order the components 50 L component (a); 50 kg component (b); 50 kg component (c); 50 kg component (d); 50 kg component (e); 50 kg component (f); and 50 kg component (g) with the foundation mixture to create a first temporary mixture, ensuring homogeneous mixing after each addition;
(V) mixing 500 kg the legume powder component with the first temporary mixture at 400 rpm for 20 minutes to create a second temporary mixture;
(VI) mixing 500 L the coenzyme Q10 component with the second temporary mixture at 400 rpm for 20 minutes to obtain a uniform mixture;
(VII) incubating the uniform mixture at 25° C.-37° C. for 10 days, adding the ginsenoside Rb1 extract component, and continuing incubation at 25° C.-37° C. for 10 days to obtain a post-incubation mixture; and
(VIII) concentrating the post-incubation mixture at 50° C. to obtain the composition 200.

The example 2 is made according to the embodiment of the present invention, the composition 300 is created by process 100 similar to Example 1 above comprising from Step (I) to Step (VIII), the difference is:
  at step (IV) the Ngoc Linh *ginseng* (*Panax vietnamensis*) extract component used is 25 liters.

The example 3 is made according to the embodiment of the present invention, the composition 400 is created by process 100 similar to Example 1 above comprising from Step (I) to Step (VIII), the difference is:
  at step (VI) the amount of Coenzyme Q10 used is 250 liters.

The example 4 is made according to the embodiment of the present invention, the composition 500 is created by process 100 similar to Example 1 above comprising from Step (I) to Step (VIII), the difference is:
  at step (VI) the amount of Coenzyme Q10 used is 375 liters.

The example 5 is made according to the embodiment of the present invention, the composition 600 is created by process 100 similar to Example 1 above comprising from Step (I) to Step (VIII), the difference is:
  at step (IV) the Ngoc Linh *ginseng* (*Panax vietnamensis*) extract component used is 37.5 liters.

Example 6 evaluating the immune-enhancing effect of the composition 200, which is obtained from the example 1 in accordance with an exemplary embodiment of the present invention.

Test subjects: the experiment was performed on healthy adult male (Swiss albino) mice, 5-6 weeks old, weighing 25±2 grams. They were nurtured to stabilize for 1 week before conducting the experiment at room temperature (27° C.-28° C.). They were fed with synthetic pellets for mice, and the drinking water was tap water.

Test sample: the composition 200 which is obtained from the example 1, and the control sample used distilled water.

Male (Swiss albino) mice were immunodeficient by intraperitoneally administering a single dose of cyclophosphamide (150 mg/kg body weight) on the first day and then orally administering the test samples continuously for 5 days.

The experiment for immune-enhancing of the composition 200 by arrangement total of 60 male mice was used for experimental (23-25 g) divided into six treatments listed in Table 5 below.

TABLE 5

Experimental plots in immunodeficient mouse model

| No. | Group | Treatments | Plot (n = 10) | Test sample | Oral dose |
|---|---|---|---|---|---|
| 1 | CY (−) | N1 | physiological control | drink distilled water | — |
| 2 | | N2 | test sample | composition 200 | 100 mg/kg/day |
| 3 | | N3 | reference drug | levamisole | 25 mg/kg |
| 4 | CY (+) | N4 | disease control | drink distilled water | — |
| 5 | | N5 | test sample | composition 200 | 100 mg/kg/day |
| 6 | | N6 | reference drug | levamisole | 25 mg/kg |

CY (−): Do not inject cyclophosphamide; CY (+): inject intraperitoneally administering a single dose of cyclophosphamide 150 mg/kg.

The Animal Ethics Committee approved this study, code 1170B/KHTN-ACUCUS.

Evaluation of Immune-Enhancing Effects Through the Following Indicators:

1) Phagocytosis Index

One hour after the fifth day's dose, mice were injected intraperitoneally into the tail vein by Parker, which has a measured density with a carbon content of 751 mg/kg. 20 µl of blood was collected from the mouse orbital venous plexus at 0 and 5 min. The blood samples were diluted in 2 ml of 0.1% sodium carbonate solution, and the optical density was measured at 640 nm. The phagocytic index was calculated using the formula:

$$K = \frac{\ln OD_1 - \ln OD_2}{T_2 - T_1}$$

wherein, K is a constant representing carbon clearance; OD1 and OD2: Optical density measured at times T1 (0 minutes) and T2 (5 minutes).

2) Relative Weight of Organs: Liver, Spleen, and Thymus

Anatomy mice were dissection and weighed the liver, spleen, and thymus on the 10th day after intraperitoneally administering a single dose of cyclophosphamide (150 mg/kg body weight), and the reference drug chosen in the experiment was levamisole at an oral dose of 25 mg/kg. The relative weights of the organs were calculated using the following formula:

$$g(\%) = \frac{P_{cq}}{P_{ct}} \times 100$$

wherein Pcq is the weight of the organ; Pct is the body weight of the mouse at the time of survey.

3) Leukocyte Count and Percentage of Leukocyte Types;

Collected tail vein blood from mice on the 5th day after CY injection. The reference drug chosen in the experiment was levamisole at a dose of 25 mg/kg.

4) Cellular Immune Response

After 1 hour of cyclophosphamide injection, mice were given to drink the test sample continuously on the following days; the reference drug chosen in the experiment was levamisole at a dose of 25 mg/kg. On the 14th day, sensitization was induced by tail vein injection with ovalbumin at a dose of 0.5 mg/kg mouse body weight. On the 18th day, ovalbumin was injected again at a dose of 2.5 mg/kg mouse body weight with an injection volume of 50 µl into the subcutaneous tissue of the right foot to determine the phagocytic index by carbon clearance experiment and to examine the cellular immune response (delayed hypersensitivity response) in the ovalbumin experiment. Measure the volume of the mouse paw at 4 hours (V1) and 24 hours (V2) after the second ovalbumin injection. The left paw that was not injected was used as the reference (Vo). Calculate the percentage of mouse paw edema using the formula:

$$\%V4 \text{ hour} = \frac{V1 - V0}{V0} \times 100, \%V24 \text{ hour} = \frac{V2 - V0}{V0} \times 100$$

The Result:
1) Phagocytosis Index

TABLE 6

The results of the phagocytic index (K) of the group experiments in accordance with exemplary embodiment of the present invention

| No. | Group | Treatments | K |
|---|---|---|---|
| 1 | CY (−) | N1 | 0.242 ± 0.032 |
| 2 | | N2 | 0.269 ± 0.029 |
| 3 | | N3 | 0.293 ± 0.026 |
| 4 | CY (+) | N4 | 0.159 ± 0.027 |
| 5 | | N5 | 0.278 ± 0.028 |
| 6 | | N6 | 0.292 ± 0.029 |

Based on Table 6:

In the CY (−) group, mice taking the composition 200 at a dose of 100 mg/kg/day, similar to levamisole at a dose of 25 mg/kg, did not affect the phagocytic index in normal mice;

In the CY (+) group, the phagocytic index after 5 minutes in the physiological control plot injected with cyclophosphamide decreased, proving that the carbon clearance experimental model was successfully created to determine the phagocytic index. The plots taking the composition 200 preparation orally, as well as the reference drug levamisole, both had an increased phagocytic index after 5 minutes.

2) Relative Weight of Organs: Liver, Spleen, and Thymus

TABLE 7

The results of the relative weight of organs: liver, spleen, and thymus of the group experiments in accordance with exemplary embodiment of the present invention

| No. | Group | Treatments | spleen (g %) | thymus (g %) | liver (g %) |
|---|---|---|---|---|---|
| 1 | CY (−) | N1 | 0.618 ± 0.084 | 0.215 ± 0.028 | 5.150 ± 0.206 |
| 2 | | N2 | 0.543 ± 0.043 | 0.259 ± 0.024 | 4.916 ± 0.107 |
| 3 | | N3 | 0.531 ± 0.046 | 0.163 ± 0.034 | 4.661 ± 0.133 |
| 4 | CY (+) | N4 | 0.337 ± 0.021 | 0.071 ± 0.011 | 4.563 ± 0.158 |
| 5 | | N5 | 0.461 ± 0.060 | 0.076 ± 0.011 | 4.966 ± 0.056 |
| 6 | | N6 | 0.343 ± 0.031 | 0.073 ± 0.013 | 5.074 ± 0.189 |

Based on Table 7:
- In the CY (−) group, mice taking the composition 200, similar to levamisole at a dose of 25 mg/kg did not affect the phagocytic relative weight of organs: liver, spleen, and thymus in normal mice;
- In the CY (+) group, the disease control plots had the relative weight of the liver, spleen, and thymus decreased (45.69%, 67.92%, and 11.40%), respectively. The plots taking the composition 200 have the relative weight of the liver and spleen increased compared to disease control, showing the effect of restoring the relative weight of spleen and liver ratio similar to levamisole at a dose of 25 mg/kg.

3) Leukocyte Count and Percentage of Leukocyte Types

TABLE 8

The results of the leukocyte count and percentage (%) of leukocyte types of the group experiments in accordance with exemplary embodiment of the present invention

| No. | Group | Treatment | Total leukocytes/mm$^3$ | % Neutrophil | % Lymphocyte | % Monocyte |
|---|---|---|---|---|---|---|
| 1 | CY (−) | N1 | 4696.00 ± 660.87 | 32.48 ± 2.46 | 46.85 ± 2.13 | 4.41 ± 1.05 |
| 2 | | N2 | 4923.00 ± 278.67 | 42.26 ± 1.20 | 43.36 ± 1.84 | 3.36 ± 0.48 |
| 3 | | N3 | 4340.00 ± 621.03 | 43.21 ± 3.99 | 41.83 ± 2.90 | 3.40 ± 0.50 |
| 4 | CY (+) | N4 | 565.00 ± 99.59 | 13.78 ± 2.95 | 43.56 ± 4.18 | 18.98 ± 1.80 |
| 5 | | N5 | 1365.00 ± 310.20 | 14.43 ± 3.13 | 39.42 ± 2.58 | 30.51 ± 3.22 |
| 6 | | N6 | 993.00 ± 144.30 | 10.81 ± 1.18 | 59.56 ± 4.42 | 14.06 ± 3.64 |

Based on Table 8:
- In the CY (−) group, the plots mice taking the composition 200 similar to levamisole at a dose of 25 mg/kg did not affect the total leukocytes, % Lymphocyte, % Monocyte; however, it increased the % Neutrophil when compared to physiological control in normal mice;
- In the CY (+) group, the disease control plots had total leukocytes, the % Neutrophil decreased, and the % Monocyte increased compared to physiological control. The plots taking the composition 200 have total leukocytes increased compared to disease control and showed the same effect of improving neutrophil ratio similar to levamisole at a dose of 25 mg/kg in a mouse model of immunodeficiency induced by cyclophosphamide. However, the plots of mice taking the composition 200 and levamisole at a dose of 25 mg/kg did not show the effect of restoring leukocyte indices to normal values when compared to physiological control.

4) Cellular Immune Response

TABLE 9

The results of the percentage of the mouse paw edema after 4 hours (% V4 h) and after 24 hours (% V24 h) of the group experiments in accordance with exemplary embodiment of the present invention;

| No. | Group | Treatments | % V$_{4h}$ | % V24 h |
|---|---|---|---|---|
| 1 | CY (−) | N1 | 79.36 ± 6.83 | 39.20 ± 6.67 |
| 2 | | N2 | 73.97 ± 8.31 | 36.42 ± 5.18 |
| 3 | | N3 | 79.63 ± 7.63 | 37.98 ± 6.39 |
| 4 | CY (+) | N4 | 54.55 ± 5.04 | 20.45 ± 3.56 |
| 5 | | N5 | 79.12 ± 4.56 | 42.15 ± 8.35 |
| 6 | | N6 | 81.27 ± 7.52 | 38.28 ± 7.12 |

Based on Table 9:
- In the CY (−) group, the plots mice taking the composition 200 similar to levamisole at a dose of 25 mg/kg did not affect the percentage of the mouse paw edema in normal mice;
- In the CY (+) group, the disease control plot had the percentage of the mouse paw edema decreased after 4 hours and after 24 hours of the second ovalbumin injection, compared to the physiological control group. The results recorded after 4 hours of the second ovalbumin injection showed that the plots of mice taking the composition 200 had increased mouse paw edema, similar to the effect of levamisole; the value of mouse paw edema returned to normal when compared to the physiological control group; the results recorded after 24 hours of the second ovalbumin injection showed that the composition 200 had increased mouse paw edema compared to the disease control group, showing an immune response effect similar to levamisole; the value of mouse paw edema returned to normal when compared to the physiological control group. This proves that composition 200 shows the effect of enhancing the hypersensitivity reaction of the cellular immune response (delayed hypersensitivity).

In summary, the results showed that the composition of 200 doses of 100 mg/kg/day showed an immune-enhancing effect through the ability to inhibit immunodeficiency manifestations in white mice immunodeficient by Cyclophosphamide, with an effect equivalent to that of levamisole at a dose of 25 mg/kg/day.

Example 7 evaluating the anti-thrombotic effect of the composition 200, which is obtained from the example 1 in accordance with an exemplary embodiment of the present invention.

Test subjects: the experiment was performed on healthy adult male (Swiss albino) mice, 5-6 weeks old, weighing 25±2 grams, tail length from 7 cm. They were nurtured to stabilize for 1 week before conducting the experiment at room temperature (27° C.-28° C.). They were fed with synthetic pellets for mice, and the drinking water was tap water.

Test sample: the composition 200 which is obtained from the example 1, and the control sample used distilled water.

Male (Swiss albino) mice were induced into thrombosis by intraperitoneally administering of k-carrageenan solution at a dose of 10 mg/kg (diluted in 0.9% NaCl) on the 7th day, 1 hour after giving the mice the last dose of the drug (the physiological control group was intraperitoneally administering with 10 ml/kg of physiological saline).

The experiment for anti-thrombotic effect of the composition 200 by arrangement total of 40 male mice was used for experimental (23-25 g) divided into four treatments listed in Table 10 below.

TABLE 10

Experimental plots in anti-thrombotic effects

| No. | Treatments | Plot (n = 10) | Test sample | Oral dose | Inject dose |
|---|---|---|---|---|---|
| 1 | A1 | Experimental model | drink distilled water inject intraperitoneally administering k-carrageenan | 0.2 mL/ 10 g/day in 7 days | 10 mg/kg on day 7 |
| 2 | A2 | aspirin control | drink aspirin inject intraperitoneally administering k-carrageenan | 25 mg/kg/day in 7 days | 10 mg/kg on day 7 |
| 3 | A3 | test sample | drink composition 200 inject intraperitoneally administering k-carrageenan | 100 mg/kg/day in 7 days | 10 mg/kg on day 7 |
| 4 | A4 | physiological control | drink distilled water inject physiological saline | 0.2 mL/ 10 g/day in 7 days | 10 mg/kg on day 7 |

Take mouse blood to test for some coagulation parameters: Platelet count (*103/μl); Fibrinogen (mg/dl); activated partial thromboplastin time (APTT) (seconds); prothrombin time (PT); and thrombin time (TT) (seconds).

The Result

1) Results of Platelet Count and Fibrinogen Evaluation in Mouse Blood

TABLE 11

Effect of composition 200 on platelet count (G/L) in mouse blood in accordance with exemplary embodiment of the present invention

| No. | Treatments | Plot (n = 10) | platelet count (G/L) |
|---|---|---|---|
| 1 | A1 | experimental model | 478.68 ± 96.64 |
| 2 | A2 | aspirin control | 459.87 ± 98.95 |
| 3 | A3 | physiological control | 472.79 ± 108.20 |
| 4 | A4 | physiological control | 634.95 ± 119.89 |

Compared with the physiological control plot, the number of platelets in the blood of mice in the experimental model plot, the plot using aspirin and the plot using composition 200 all decreased.

Compared with the experimental model plot, the number of platelets in the blood of mice in the plot using aspirin and the plot using composition 200 on white mice both decreased.

Compared with the control plot using aspirin, the number of platelets in the blood of mice in the plot using composition 200 had similar results.

TABLE 12

Effect of composition 200 on Fibrinogen (mg/L) in mouse blood in accordance with exemplary embodiment of the present invention

| No. | Treatments | Plot (n = 10) | platelet count (G/L) |
|---|---|---|---|
| 1 | A1 | experimental model | 3.43 ± 0.11 |
| 2 | A2 | aspirin control | 2.58 ± 0.07 |
| 3 | A3 | test sample | 2.83 ± 0.08 |
| 4 | A4 | physiological control | 1.85 ± 0.05 |

Compared with the physiological control plot, the Fibrinogen in the blood of mice in the experimental model plot, the plot using aspirin and the plot using composition 200 all increased.

Compared with the experimental model plot, the Fibrinogen in the blood of mice in the plot using aspirin and the plot using composition 200 on white mice both decreased.

Compared with the control plot using aspirin, the Fibrinogen in the blood of mice in the plot using composition 200 had bigger results.

TABLE 13

Effect of composition 200 on activated partial thromboplastin time (APTT) (seconds); prothrombin time (PT) (seconds); and thrombin time (TT) (seconds) in accordance with exemplary embodiment of the present invention

| No. | Treatments | Plot (n = 10) | APTT (seconds) | PT (seconds) | TT (seconds) |
|---|---|---|---|---|---|
| 1 | A1 | experimental model | 32.56 ± 0.38 | 14.30 ± 0.44 | 15.84 ± 0.27 |
| 2 | A2 | aspirin control | 36.54 ± 0.31 | 17.32 ± 0.37 | 18.67 ± 0.51 |
| 3 | A3 | test sample | 35.77 ± 0.37 | 16.99 ± 0.42 | 18.22 ± 0.40 |
| 4 | A4 | physiological control | 37.98 ± 0.39 | 18.93 ± 0.40 | 20.36 ± 0.45 |

Compared with the physiological control plot, the activated partial thromboplastin time (APTT) in the experimental model plot, the plot using aspirin and the plot using composition 200 all decreased. Compared with the experimental model plot, the activated partial thromboplastin time (APTT) in the plot using aspirin and the plot using composition 200 on white mice both increased. Compared with the control plot using aspirin, the activated partial thromboplastin time (APTT) in the plot using composition 200 had similar results.

Compared with the physiological control plot, the prothrombin time (PT) in the experimental model plot, the plot using aspirin and the plot using composition 200 all decreased. Compared with the experimental model plot, the prothrombin time (PT) in the plot using aspirin and the plot using composition 200 on white mice both increased. Compared with the control plot using aspirin, the prothrombin time (PT) in the plot using composition 200 had smaller but not significant results.

Compared with the physiological control plot, the thrombin time (TT) in the experimental model plot, the plot using aspirin and the plot using composition 200 all decreased. Compared with the experimental model plot, the thrombin time (TT) in the plot using aspirin and the plot using composition 200 on white mice both increased. Compared with the control plot using aspirin, the thrombin time (TT) in the plot using composition 200 had similar results.

In summary, the results showed that the composition 200 at a dose of 100 mg/kg/day showed antithrombotic effects on mice induced into thrombosis by intraperitoneally administering of k-carrageenan had an effect equivalent to aspirin at a dose of 25 mg/kg/day.

Example 8 evaluating the hematological parameters effect of the composition 200, which is obtained from the example 1 in accordance with an exemplary embodiment of the present invention.

Test subjects: the experiment was performed on healthy adult white rats, both sexes, weighing 170±20 grams. They were nurtured to stabilize for 1 week before conducting the experiment at room temperature (27° C.-28° C.). They were fed with synthetic pellets for mice, and the drinking water was tap water.

Test sample: the composition 200 which is obtained from the example 1, and the control sample used distilled water.

The experiment evaluated the hematological parameters effect of the composition 200 by arranging 40 mice divided into two treatments; the trial period is 60 days, as listed in Table 14 below.

TABLE 14

Experimental plots in hematological parameters effects

| No. | Treatments | Plot (n = 20) | Test sample | Oral dose |
|---|---|---|---|---|
| 1 | B1 | physiological control | drink distilled water | 5 mL/kg/day |
| 2 | B2 | test sample | composition 200 | 100 mg/kg/day |

Take mouse blood to test for at the time points before oral, after 30 days oral, and after 60 days oral. The parameters included: Red blood cell count (T/L); Hemoglobin (Hb, g/dL); Hematocrit (%); White blood cell count (GIL) and platelet count (G/L); and mean corpuscular volume (MCV, fL).

The Result:

The results of the evaluation of the effect on hematological parameters of the composition 200 are listed in Table 15 below.

TABLE 15

Effect of composition 200 on hematological parameters in mouse in accordance with exemplary embodiment of the present invention

| parameters | the time points | physiological control (n = 20) | test sample (n = 20) |
|---|---|---|---|
| Red blood cell (T/L) | before oral | 7.00 ± 0.50 | 7.00 ± 0.50 |
|  | after 30 days oral | 7.05 ± 0.55 | 7.20 ± 0.48 |
|  | after 60 days oral | 7.08 ± 0.52 | 7.30 ± 0.50 |
| Hemoglobin (g/dL) | before oral | 13.00 ± 0.80 | 13.00 ± 0.80 |
|  | after 30 days oral | 13.05 ± 0.76 | 13.50 ± 0.78 |
|  | after 60 days oral | 13.10 ± 0.78 | 13.60 ± 0.75 |
| Hematocrit (%) | before oral | 42.00 ± 2.00 | 42.00 ± 2.00 |
|  | after 30 days oral | 42.10 ± 1.95 | 43.50 ± 2.10 |
|  | after 60 days oral | 42.20 ± 2.05 | 44.00 ± 2.00 |
| MCV (fL) | before oral | 60.00 ± 3.00 | 60.00 ± 3.00 |
|  | after 30 days oral | 60.10 ± 2.80 | 61.50 ± 2.90 |
|  | after 60 days oral | 60.20 ± 2.85 | 62.00 ± 2.80 |
| White blood cell (G/L) | before oral | 7.00 ± 1.00 | 7.00 ± 1.00 |
|  | after 30 days oral | 7.05 ± 1.05 | 7.20 ± 1.08 |
|  | after 60 days oral | 7.10 ± 1.10 | 7.50 ± 1.12 |
| platelet (G/L) | before oral | 550 ± 90 | 550 ± 90 |
|  | after 30 days oral | 555 ± 85 | 580 ± 88 |
|  | after 60 days oral | 560 ± 82 | 600 ± 85 |

The experimental results in Table 15 show that composition 200 positively affects hematological parameters in mice after 60 days of use. Specifically, red blood cell count increased from 7.00±0.50 T/L (before oral) to 7.30±0.50 T/L, and the hemoglobin increased from 13.00±0.80 g/dL to 13.60±0.75 g/dL, higher than the physiological control plot (7.08±0.52 T/L and 13.10±0.78 g/dL). Hematocrit increased from 42.00±2.00% to 44.00±2.00%, while the physiological control plot only increased slightly to 42.20±2.05%. Mean corpuscular volume (MCV) increased from 60.00±3.00 fL to 62.00±2.80 fL, and the white blood cell count increased from 7.00±1.00 G/L to 7.50±1.12 G/L, higher than that of the physiological control plot (7.10±1.10 G/L). Platelet count also increased from 550±90 G/L to 600±85 G/L, significantly higher than that of the physiological control plot (560±82 G/L). These results confirm that composition 200 is safe and can improve hematological indices and support health and the immune system.

Example 9 evaluating the erythroid parameters in patients 1, 2, and 3 treated with supportive use of composition 200, which is obtained from the example 1 in accordance with an exemplary embodiment of the present invention.

Patients 1:

Based on the patient's medical records, the patient was diagnosed: severe chronic anemia (D64)—iron deficiency anemia (D50)—thalasseamia (D56)—adenomyosis—bilateral ovarian cysts;

During the treatment period according to the hospital's regimen, the patient supportive use of composition 200. After 16 months of treatment, the patient had tests done on changes in erythroid parameters: red blood cell count (RBC), hemoglobin (HGB), hematocrit (HCT), mean corpuscular volume (MCV), mean corpuscular hemoglobin (MCH), red blood cell diameter distribution width (RDW) in whole blood. The results are listed in Table 16 below.

TABLE 16

Change trend of erythroid parameters of patient 1 before and after treated with supportive use of composition 200

| No. | parameters | Unit | Time of test 4 Mar. 2022 | Time of test 28 Jul. 2023 |
|---|---|---|---|---|
| 1 | RBC | M/µL | 3.77 | 5.36 |
| 2 | HGB | g/dL | 12.4 | 13.3 |
| 3 | HCT | % | 38.7 | 40.6 |
| 4 | MCV | fl | 74.1 | 75.7 |
| 5 | MCH | pg | 24.5 | 24.7 |
| 6 | RDW | % | 19.08 | 13.7 |

Referring to Table 16, show that the erythroid parameters all increased, including: red blood cell count (RBC) from 3.77 M/µL increased to 5.36 M/µL, hemoglobin (HGB) from 12.4 g/dL increased to 13.3 g/dL, hematocrit (HCT) from 38.7% increased to 40.6%, mean corpuscular volume (MCV) from 74.1 fL increased to 75.7 fL, mean corpuscular hemoglobin (MCH) from 24.5 pg increased to 24.7 pg, and red blood cell diameter distribution width (RDW) from 19.08% at high level decreased to 13.7%.

Patients 2:

Based on the patient's medical records, the patient was diagnosed: severe chronic anemia (D64).

During the treatment period according to the hospital's regimen, the patient supportive use of composition 200. After 10 months of treatment, the patient had tests done on changes in erythroid parameters: red blood cell count (RBC), hemoglobin (HGB), hematocrit (HCT), mean corpuscular volume (MCV), mean corpuscular hemoglobin (MCH), red blood cell diameter distribution width (RDW) in whole blood. The results are listed in Table 17 below.

TABLE 17

Change trend of erythroid parameters of patient 2 before and after treated with supportive use of composition 200

| No. | parameters | Unit | Time of test 2 Jul. 2022 | Time of test 11 May 2023 |
|---|---|---|---|---|
| 1 | RBC | M/pL | 3.84 | 3.99 |
| 2 | HGB | g/dL | 9.4 | 11.0 |
| 3 | HCT | % | 29.8 | 34.0 |
| 4 | MCV | fl | 74.8 | 88.5 |
| 5 | MCH | pg | 23.5 | 28.7 |
| 6 | RDW | % | 14.0 | 15.8 |

Referring to Table 17, show that the erythroid parameters all increased, including: red blood cell count (RBC) increased from 3.84 M/µL to 3.99 M/µL, hemoglobin (HGB) increased from 9.4 g/dL to 11.0 g/dL, hematocrit (HCT) increased from 29.8% to 34.0%, mean corpuscular volume (MCV) increased from 74.8 fL to 88.5 fL, mean corpuscular hemoglobin (MCH) increased from 23.5 pg to 28.7 pg, and red cell diameter distribution width (RDW) decreased from 14.0% at high levels to 15.8%.

Patients 3:

Based on the patient's medical records, the patient was diagnosed: severe chronic anemia (D64);

During the treatment period according to the hospital's regimen, the patient supportive use of composition 200. After 12 months of treatment, the patient had tests done on changes in erythroid parameters: red blood cell count (RBC), hemoglobin (HGB), hematocrit (HCT), mean corpuscular volume (MCV), mean corpuscular hemoglobin (MCH), red blood cell diameter distribution width (RDW) in whole blood. The results are listed in Table 18 below.

TABLE 18

Change trend of erythroid parameters of patient 3 before and after treated with supportive use of composition 200

| No. | parameters | Unit | Time of test 10 Feb. 2022 | Time of test 25 Feb. 2023 |
|---|---|---|---|---|
| 1 | RBC | M/pL | 3.56 | 3.89 |
| 2 | HGB | g/dL | 11.6 | 12.3 |
| 3 | HCT | % | 36.2 | 38.5 |
| 4 | MCV | fl | 74.3 | 75.6 |
| 5 | MCH | pg | 24.1 | 24.8 |
| 6 | RDW | % | 18.2 | 15.7 |

Referring to Table 18, show that the erythroid parameters all increased, including: red blood cell count (RBC) increased from 3.56 M/µL to 3.89 M/µL, hemoglobin (HGB) increased from 11.6 g/dL to 12.3 g/dL, hematocrit (HCT) increased from 36.2% to 38.5%, mean corpuscular volume (MCV) increased from 74.3 fL to 75.6 fL, mean corpuscular hemoglobin (MCH) increased from 24.1 pg to 24.8 pg, and red cell diameter distribution width (RDW) decreased from 18.2% to 15.7%.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for producing a plant-based extract composition having the effect of enhancing nutrition and immunity, comprising the following steps (i) to (viii):
   (i) preparing materials including:
      (a) a Ngoc Linh *ginseng* extract component having a predetermined first percentage (%) by weight, prepared by mixing a first extract and a second extract at a ratio of 2:(0.05-1) v/v;
      wherein the first extract is prepared by performing steps (a1) to (c1), comprising:
         (a1) preparing material: collecting Ngoc Linh *ginseng* roots aged 3-5 years, cleaning, cutting into pieces, drying to a moisture content below 15%, grinding, and sieving through a 0.5-1 mm mesh to obtain a first powder;
         (b1) extracting the first powder with saturated n-butanol (n-BuOH) solution at a ratio of 1:20 w/v for 1 hour, followed by ultrasonic-assisted extraction at a frequency of 35 kHz for 2 hours, wherein step (b1) is repeated three times to obtain a first temporary extract; and
         (c1) removing the solvent from the first temporary extract and centrifuging at a speed of 1000-5000 rpm for 10 minutes to obtain the first extract;
      wherein the second extract is prepared by performing steps (a2) to (d2), comprising:
         (a2) preparing material: collecting the stems and leaves of the Ngoc Linh *ginseng* aged 3-5 years, cleaning, cutting into pieces, drying to a moisture content below 15%, grinding, and sieving through a 0.5-1 mm mesh to obtain a second powder;
         (b2) extracting the second powder with 70% ethanol solution at a ratio of 1:8 w/v for 2 days, then filtering to obtain a second temporary extract and a first residue;

(c2) extracting the first residue with 70% ethanol solution at a ratio of 1:2 w/v using ultrasonic-assisted extraction at a frequency of 35 kHz for 3 hours, then filtering to obtain a third temporary extract; and (d2) mixing the second temporary extract with the third temporary extract, removing the solvent, and filtering to obtain the second extract;

(b) a jiaogulan powder component having a predetermined second percentage (%) by weight, prepared by cleaning leaves and stems of the *Gynostemma pentaphyllum*, cold-drying at 30° C.-31° C. until the moisture reaches 5%-7%, then grinding and sieving through a 0.5-1 mm mesh to obtain the jiaogulan powder component;

(c) a maingay's tree powder component having a predetermined third percentage (%) by weight, prepared by cleaning the *Cratoxylum maingayi* leaves, drying at 50° C.-60° C. until the moisture reaches 5%-7%, then grinding and sieving through a 0.5-1 mm mesh to obtain maingay's tree powder component;

(d) a nodding clubmoss powder component having a predetermined fourth percentage (%) by weight, prepared by cleaning the entire plant of the *Lycopodiella cernua*, drying at 50° C.-60° C. until moisture reaches 5%-7%, then grinding and sieving through a 0.5-1 mm mesh to obtain the nodding clummoss powder component;

(e) a red *ginseng* powder component having a predetermined fifth percentage (%) by weight, prepared by cleaning red *ginseng* roots, drying in three stages, then grinding and sieving through a 0.5-1 mm mesh to obtain the red *ginseng* powder component; wherein drying in three stages includes:
a first stage: drying at 40° C. for 24 hours:
a second stage: drying at 50° C. for 48 hours; and
a third stage: drying at 60° C. until the moisture reaches 5%-7%;

(f) a *codonopsis* root powder component having a predetermined sixth percentage (%) by weight, prepared by cleaning the *Codonopsis* root, cutting into 0.5-1 cm pieces, drying at 60° C. until the moisture reaches 5%-7%, then grinding and sieving through a 0.5-1 mm mesh to obtain the *codonopsis* root powder component;

(g) an *angelica* root powder component having a predetermined seventh percentage (%) by weight, prepared by cleaning the *Angelica* root, drying at 30° C.-35° C. until the moisture reaches 5%-7%, then grinding and sieving through a 0.5-1 mm mesh to obtain the *angelica* root powder component;

(h) a rice bran oil component having a predetermined eighth percentage (%) by weight, extracted from germ and inner bran layer of rice using water-assisted ultrasonic extraction at 50° C. for 30 minutes with a stirring speed of 1000 rpm and a rice bran-to-water ratio of 1.5:10; ultrasonic treatment is conducted for 70 minutes at 25° C. to obtain the rice bran oil component;

(i) a legume powder component having a predetermined ninth percentage (%) by weight, including 1 part red bean, 1 part black bean, 1 part green bean, 1 part soybean, and 1 part white bean;

(j) a coenzyme Q10 component having a predetermined tenth percentage (%) by weight, extracted from a royal jelly by performing steps (A) to (F):

(A) preparing the royal jelly obtained from honeybees selected from one or more species with genbank identifiers including: KM066965.1, KM066964.1, KM066963.1, KM066960.1, KM066951.1, KM066962.1, KM066959.1, KM066957.1, KM066961.1, KM066952.1, KM066955.1, KM066956.1, KM066958.1, KM066953.1, and KM066954.1;

(B) mixing 0.5 g of the royal jelly with 1 mL of methanol and 1 mL of n-hexane in a 10 mL test tube, shaking the test tube for 2 minutes, and subjecting it to ultrasonic treatment at a frequency of 35 kHz for 30 minutes to obtain a mixed solution;

(C) centrifuging the mixed solution at 2500 rpm for 15 minutes, then filtering to obtain a filtered solution;

(D) centrifuging the filtered solution for 5 minutes at 4500 rpm to obtain a first solution;

(E) mixing the first solution with 1 mL of n-hexane and another 1 mL of n-hexane in a 10 mL test tube, shaking the test tube for 2 minutes, and subjecting it to ultrasonic treatment at a frequency of 35 kHz for 30 minutes, repeating step (E) twice to obtain a second solution; and (F) concentrating the second solution using inert gas nitrogen to obtain the coenzyme Q10 component;

(k) a ginsenoside Rb1 extract component having a predetermined eleventh percentage (%) by weight, prepared by performing steps (a3) to (g3), including:

(a3) preparing material: obtaining a *Panax notoginseng* roots aged 3 to 7 years, washing them clean, cutting into small pieces, and drying to a moisture content of less than 15%;

(b3) extracting the material with 60% ethanol solvent at a ratio of 1:6 w/v using an ultrasonic extraction device at 60° C. for 2 hours, repeating step (b3) three times to obtain a fourth temporary extract;

(c3) filtering the fourth temporary extract and removing the solvent to obtain an extract concentrate;

(d3) dissolving the extract concentrate in distilled water at a ratio of 1:6 w/v to obtain a fifth temporary extract;

(e3) adding n-butanol solution and the fifth temporary extract at a ratio of 2:1 v/v to an ultrasonic extraction device at 60° C. for 2 hours, repeating step (e3) three times to obtain a n-butanol fraction and distilling the solvent under reduced pressure to obtain a sixth temporary extract;

(f3) centrifuging the sixth temporary extract at 5000 rpm for 10 minutes to obtain a precipitate; and (g3) drying the precipitate at 75° C. for 3-8 hours to obtain the ginsenoside Rb1 extract component;

(l) the remainder is a honey component having a predetermined twelfth percentage (%) by weight;

wherein the total weight percentage from the first to the twelfth components equals 100% by weight;

(ii) creating a base mixture by heating the honey component at 60° C.-65° C., stirring at 300-500 rpm for 30 minutes;

(iii) creating a foundation mixture by homogenizing the rice bran oil with the base mixture at step (ii), stirring at 300-500 rpm, and heating for an additional 2-5 minutes;

(iv) mixing the components (a) to (g) in order with the foundation mixture at step (iii) to create a first temporary mixture, ensuring homogeneous mixing after each addition;

(v) mixing the legume powder component with the first temporary mixture at step (iv) at 300-500 rpm for 20 minutes to create a second temporary mixture;

(vi) mixing the coenzyme Q10 component with the second temporary mixture at step (v) at 300-500 rpm for 20 minutes to obtain a uniform mixture;

(vii) incubating the uniform mixture at 25° C.-37° C. for 10-15 days, adding the ginsenoside Rb1 extract component, and continuing incubation at 25° C.-37° C. for 10-15 days to obtain a post-incubation mixture; and (viii) concentrating the post-incubation mixture at 50° C. to obtain the plant-based extract composition having the effect of enhancing nutrition and immunity.

2. The method according to claim 1, wherein the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) to make up 100%.

3. The method according to claim 1, wherein the predetermined first percentage (%) by weight is 0.5%-1%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) to make up 100%.

4. The method according to claim 1, wherein the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 8%-10%, the predetermined eleventh percentage (%) by weight is 1.5%-2%, and the remainder is the twelfth percentage (%) to make up 100%.

5. The method according to claim 1, wherein the predetermined first percentage (%) by weight is 1.5%-2%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 12%-13%, the predetermined eleventh percentage (%) by weight is 1.5%-2%, and the remainder is the twelfth percentage (%) to make up 100%.

6. The method according to claim 1, wherein the predetermined first percentage (%) by weight is 1.2%-1.4%, the predetermined second percentage (%) by weight is 1.5%-2%, the predetermined third percentage (%) by weight is 1.5%-2%, the predetermined fourth percentage (%) by weight is 1.5%-2%, the predetermined fifth percentage (%) by weight is 1.5%-2%, the predetermined sixth percentage (%) by weight is 1.5%-2%, the predetermined seventh percentage (%) by weight is 1.5%-2%, the predetermined eighth percentage (%) by weight is 15%-20%, the predetermined ninth percentage (%) by weight is 15%-20%, the predetermined tenth percentage (%) by weight is 15%-20%, the predetermined eleventh percentage (%) by weight is 1.5%-2%, and the remainder is the twelfth percentage (%) to make up 100%.

* * * * *